United States Patent
Hartung et al.

(10) Patent No.: US 8,993,792 B2
(45) Date of Patent: Mar. 31, 2015

(54) POLYGLYCOL ETHER-FREE SULPHOSUCCINATES BASED ON POLYGLYCEROL PARTIAL ESTERS AND USE THEREOF

(71) Applicants: Christian Hartung, Essen (DE); Dominik Schuch, Haan (DE); Wolfgang Berkels, Bottrop (DE); Peter Muss, Essen (DE); Ursula Westerholt, Essen (DE); Sascha Herrwerth, Essen (DE); Joerg Peggau, Essen (DE); Oliver Springer, Wesel (DE); Hans Henning Wenk, Muelheim an der Ruhr (DE); Ralf Klein, Velbert (DE)

(72) Inventors: Christian Hartung, Essen (DE); Dominik Schuch, Haan (DE); Wolfgang Berkels, Bottrop (DE); Peter Muss, Essen (DE); Ursula Westerholt, Essen (DE); Sascha Herrwerth, Essen (DE); Joerg Peggau, Essen (DE); Oliver Springer, Wesel (DE); Hans Henning Wenk, Muelheim an der Ruhr (DE); Ralf Klein, Velbert (DE)

(73) Assignee: Evonik Industries AG, Essen (DE)

( * ) Notice: Subject to any disclaimer, the term of this patent is extended or adjusted under 35 U.S.C. 154(b) by 188 days.

(21) Appl. No.: 13/758,513

(22) Filed: Feb. 4, 2013

(65) Prior Publication Data

US 2013/0204021 A1 Aug. 8, 2013

Related U.S. Application Data

(60) Provisional application No. 61/594,620, filed on Feb. 3, 2012.

(51) Int. Cl.
  *C07C 309/17* (2006.01)
  *C07C 303/32* (2006.01)
  *C07C 303/02* (2006.01)

(52) U.S. Cl.
  CPC .............. *C07C 309/17* (2013.01); *C07C 303/32* (2013.01); *C07C 303/02* (2013.01)
  USPC ............................................ 554/92; 560/151

(58) Field of Classification Search
  None
  See application file for complete search history.

(56) References Cited

U.S. PATENT DOCUMENTS

| 4,250,050 | A | 2/1981 | Asbeck et al. |
| 4,299,975 | A | 11/1981 | Asbeck et al. |
| 7,439,220 | B2 | 10/2008 | Falkowski et al. |
| 2009/0042766 | A1 | 2/2009 | Mayer et al. |
| 2011/0091399 | A1 | 4/2011 | Meyer et al. |

FOREIGN PATENT DOCUMENTS

| CA | 2104387 | | 10/1992 | |
| CA | 2199067 | * | 9/1997 | ............ C07C 309/17 |
| DE | 2700072 | | 7/1978 | |
| DE | 102005012479 A1 | | 9/2006 | |
| EP | 0794173 A2 | | 9/1997 | |
| EP | 2273966 A | | 1/2011 | |
| SU | 1330130 A1 | | 12/1985 | |
| WO | WO9218470 | | 10/1992 | |
| WO | WO2007115872 A1 | | 10/2007 | |
| WO | WO2009138306 A1 | | 11/2009 | |

OTHER PUBLICATIONS

Schrader, K. et al., "Grundlagen and Rezepturen der Kosmetika" ["Principles and Formulations of Cosmetics"], 1989, 2nd edition, p. 329 to 341, Hüthig Buch Verlag Heidelberg.
Cassel, S. et al., "Original Synthesis of Linear, Branched and Cyclic Oligoglycerol Standards", European Journal of Organic Chemistry, Mar. 2001, vol. 2001, Issue 5, pp. 875-896.
Jakobson, V.G., et al., "Diglycerol and Higher Oligomers of Glycerol as Components for Synthesis", Fette, Seifen, Anstrichmittel, 1986, pp. 101-105, No. 3, 88, English-language abstract only.
Pape, J. W. W., et al., "Validation of the Red Blood Cell Test System As in Vitro Assay for the Rapid Screening of Irritation Potential of Surfactants", Mol. Toxicol., 1987-1988 Fall, pp. 525-536, 1(4).
Chemical Abstracts, Chemi, vol. 91, Dec. 10, 1979, p. 96, database accession No. 194959s.

* cited by examiner

*Primary Examiner* — Yate K Cutliff
(74) *Attorney, Agent, or Firm* — Scully, Scott, Murphy & Presser, P.C.

(57) ABSTRACT

The invention relates to polyglycol ether-free, polyglycerol partial ester-based sulphosuccinates, the preparation thereof, and the use of these in cosmetic formulations and also in cleaning compositions in the industrial and domestic sector and formulations comprising these sulphosuccinates.

18 Claims, No Drawings

POLYGLYCOL ETHER-FREE SULPHOSUCCINATES BASED ON POLYGLYCEROL PARTIAL ESTERS AND USE THEREOF

RELATED APPLICATION

This application claims benefit to U.S. Provisional Application Ser. No. 61/594,620, filed Feb. 3, 2012, the entire content of which is incorporated herein by reference.

FIELD OF THE INVENTION

The invention relates to polyglycol ether-free, polyglycerol partial ester-based sulphosuccinates, the preparation thereof, and the use of these in cosmetic formulations and also in cleaning compositions in the industrial and domestic sector. The invention also relates to formulations comprising these sulphosuccinates.

PRIOR ART

Sulphosuccinates are much used secondary surfactants. Sulphosuccinates are used primarily on account of their good skin compatibility (mildness) and very good foaming properties, e.g., in baby shampoos and in cleaning compositions for sensitive skin.

Sulphosuccinates are used substantially as alkoxylated, in particular ethoxylated, products. A standard product on the market is Disodium Laureth Sulphosuccinate (e.g., available under the name "REWOPOL® SB FA 30 B" from Evonik Industries AG). Non-ethoxylated surfactants (e.g., Disodium Lauryl Sulphate or Disodium Lauryl Sulphosuccinate) usually have the disadvantages that they have more irritative properties compared to the corresponding alkoxylated derivatives and are often solids, something which hinders processability.

WO1992018470 describes sulphosuccinates based on ethoxylated monoglyceryl fatty acid esters and the preparation and use thereof in, for example, cosmetic cleaning compositions.

DE102005012479 claims the use of sulphosuccinates based on partial (mono)glycerides as anionic softeners.

The specifications EP0794173 and SU1330130 describe polyglycerol ester-based sulphosuccinates and the use thereof as surfactants for cleaning compositions. The described products are very mild and form stable formulations with a good foaming ability and skin feel. The products described in these specifications all have a degree of esterification of the polyglycerol with the fatty acid of at least 1, i.e., each mole equivalent of polyglycerol has been esterified with at least one mole equivalent of fatty acid. As regards the storage stability of the sulphosuccinate products and the thickenability of the formulations produced with these products, however, no statements are made.

A disadvantage of the comparatively mild sulphosuccinates described in the prior art is that they are really predominantly alkoxylated, in particular ethoxylated, products. The general market trend, particularly in the cosmetics industry, however, is nowadays towards polyglycol ether-free products.

Furthermore, the ethoxylated standard product Disodium Laureth Sulphosuccinate in the RBC test (Red Blood Cell test) with L/D values of just below 10 is still classed as moderately irritative. However, even milder and thus polyglycol ether-free products are demanded by the market and consumers.

A disadvantage of the polyglycerol ester-based sulphosuccinates described in EP0794173 (and SU1330130) is that, being concentrated aqueous solutions with a dry content of at least 30%, they do not produce clear, homogeneous and storage-stable products, but form cloudy dispersions which rapidly separate into two phases (see Examples 2.8 and 2.9). Moreover, the surfactant properties of the aqueous solutions having surface tensions of up to a minimum of ca. 33 mN/m can only be classified as average.

Also, all of the commercially available aqueous sulphosuccinates known hitherto, including the ethoxylated products, are generally not storage-stable over prolonged periods (i.e., >12 months at 25° C.) or after freeze-thaw cycles (freezing to −15° C. and allowing to thaw again to 20° C.). Multi-phase mixtures are then formed.

Moreover, sulphosuccinates used hitherto fundamentally have disadvantages when thickening the surface-active formulations produced therewith since they require large amounts of thickeners and the use of NaCl is often not possible.

It was an object of the present invention to provide extremely mild, cleaning-active surfactants.

SUMMARY OF THE INVENTION

Surprisingly, it has been found that the sulphosuccinates based on polyglycerol partial esters described below overcome the disadvantages of the prior art and thus enable the problem set by the invention to be solved.

The present invention therefore provides certain polyglycol ether-free sulphosuccinates derived from polyglycerol partial esters and of general formula I (to be described in greater detail herein below), a process for the preparation of polyglycol ether-free sulphosuccinates based on polyglycerol partial esters, and the use thereof for producing formulations. Formulations comprising the sulphosuccinates according to the invention are also provided by the invention.

One advantage of the present invention is that the sulphosuccinates according to the invention have a very reduced irritation potential in the order of magnitude of L/D ≥100 in an RBC test.

Another advantage of the sulphosuccinates according to the invention is that they have a very high surface activity, such that their aqueous solutions have surface tensions of <33 mN/m.

It is a further advantage of the sulphosuccinates according to the invention that they are free from polyglycol ether.

A further advantage of the sulphosuccinates according to the invention is that they produce readily thickenable formulations. In particular, NaCl can also sometimes be used in them as thickener.

A further advantage of the sulphosuccinates according to the invention is that they have good foam properties.

Another advantage of the sulphosuccinates according to the invention is that they form clear, homogeneous aqueous solutions.

A further advantage of the sulphosuccinates according to the invention is that they can be synthesized as highly concentrated aqueous sulphosuccinate surfactants with a dry content of >55% by weight using a simple process.

A further advantage of the sulphosuccinates according to the invention is the high storage stability of their highly concentrated aqueous solutions and of the formulations comprising these.

It is a further advantage that the sulphosuccinates according to the invention are based on natural renewable raw materials and are readily biodegradable.

It is also an advantage that the sulphosuccinates according to the invention enhance the emollient properties of the formulations on the skin as well as the care and cleaning effect of formulations for the home and industry.

DETAILED DESCRIPTION

The present invention, which provides polyglycol ether-free sulphosuccinates derived from polyglycerol partial esters and of general formula I, a process for the preparation of polyglycol ether-free sulphosuccinates based on polyglycerol partial esters, the use thereof for producing formulations, and the formulations themselves, will now be described in greater detail.

The present invention provides polyglycerol partial ester-based sulphosuccinates of general formula I

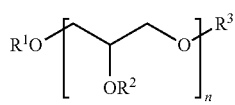

general formula I where

R$^1$, R$^2$, R$^3$=independently of one another, identical or different H, R$^4$ or R$^5$, R$^4$=a saturated or partially unsaturated acyl radical containing 6-22 carbon atoms which can be substituted by hydroxyl groups, preferably an acyl radical having 8-18 carbon atoms, in particular a capryloyl, caproyl or lauroyl radical, where mixtures of acyl radicals may also be present, R$^5$=selected from sulphosuccinic acid radicals of the formula IIa or IIb

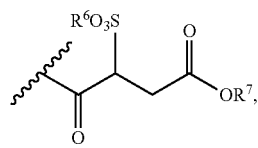

Formula IIa

Formula IIb sulphomethylsuccinic acid radicals of the formula IIc or IId

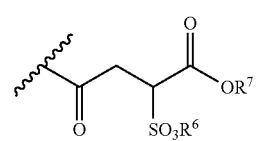

Formula IIc

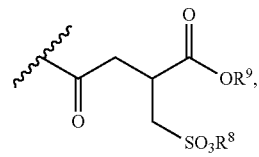

Formula IId where

R$^6$, R$^7$, R$^8$, R$^9$=independently of one another, identical or different H, an alkali metal or ½ alkaline earth metal or an ammonium group, preferably sodium, n=2 to 16, characterized in that on statistical average, per molecule of the general formula I, 0.2 to 0.8, preferably 0.3 to 0.6, radicals R$^4$ and on statistical average, per molecule of the general formula I, 0.3 to 6, preferably 0.5 to 5, particularly preferably 0.7 to 3, radicals R$^5$ are present.

Sulphosuccinates of general formula I preferred according to the invention are characterized in that, on statistical average, they have a weight ratio of carboxylic acid R$^4$OH used to polyglycerol used (i.e., general formula I where R$^1$, R$^2$, R$^3$=H) of 0.10:1 to 0.50:1, in particular from 0.15:1 to 0.40:1.

A person skilled in the art is aware that the polyglycerol basic backbone present in general formula I constitutes a statistical mixture of different compounds on account of its polymeric property. Polyglycerol can have developed ether bonds between two primary, one primary and one secondary, and also two secondary positions of the glycerol monomers. For this reason, the polyglycerol backbone usually does not exclusively consist of linearly linked glycerol units, but can also contain branches and cycles. For details, see e.g., "*Original synthesis of linear, branched and cyclic oligoglycerol standards*", Cassel et al., *J. Org. Chem.* 2001, 875-896.

Corresponding structures are also included by general formula I and are simplified in this respect.

The fatty acid radicals R$^4$ and the radicals R$^5$ can be bonded statistically to the polyglycerol backbone either via primary or via secondary hydroxyl groups.

The term "sulphosuccinate" in connection with the present compound refers to the succinic acid-based sulphosuccinates and to the itaconic acid-based sulphomethylsuccinates.

Unless stated otherwise, all conditions such as, for example, pressure and temperature are standard conditions (20° C., 1 bar). Unless described otherwise, percentages are given in mass per cent.

Sulphosuccinates of the general formula I preferred according to the invention are characterized in that they have an average degree of polymerization n of 2.5 to 12, particularly preferably from 3 to 8.

The degree of polymerization n can be determined by ascertaining the hydroxyl number of the polyglycerol used for the synthesis of the sulphosuccinate according to the invention, the average degree of polymerization n being related to the hydroxyl number of the underlying polyglycerol via the following equation:

$$n = \frac{\frac{2000 \cdot M(KOH)}{OHN} - M(Water)}{\left[M(Glycerol) - M(Water)\right] - \frac{1000 \cdot M(KOH)}{OHN}}$$

where M=molar mass; OHN=hydroxyl number of the free polyglycerol.

Alternatively, the degree of polymerization n can also be determined by ascertaining the hydroxyl number of the polyglycerol obtained following complete hydrolysis of the sulphosuccinate.

Suitable determination methods for ascertaining the hydroxyl number are in particular those according to DGF C-V 17 a (53), Ph. Eur. 2.5.3 Method A and DIN 53240.

Sulphosuccinates of the general formula I preferred according to the invention are characterized in that $R^4$=the acyl radical of one or more natural fatty acids having 8-18 carbon atoms, in particular an acyl radical of the fatty acids selected from oenanthic acid, caprylic acid, pelargonic acid, capric acid, lauric acid, myristic acid, pentadecanoic acid, palmitic acid, margaric acid, stearic acid, undecylenic acid, myristoleic acid, palmitoleic acid, petroselic acid, oleic acid, elaidic acid, vaccenic acid, linoleic acid, α-linolenic acid, γ-linolenic acid, calendic acid, punicic acid, α-elaeostearic acid, β-elaeostearic acid and mixtures thereof, where caprylic, capric or lauric acid, in particular mixtures thereof, and coconut fatty acid mixtures are particularly preferred.

According to the invention, $R^4$ can be formed by mixtures of corresponding carboxylic acids, particular preference being given here to coconut fatty acid mixtures and technical-grade cuts thereof.

Sulphosuccinates of the general formula I preferred according to the invention are characterized in that $R^5$ is selected from sulphosuccinic acid radicals of the formula IIa or IIb.

In one alternative embodiment according to the invention, preferred sulphosuccinates are of the general formula I characterized in that $R^5$ is selected from sulphomethylsuccinic acid radicals of the formula IIc or IId.

Sulphosuccinates of the general formula I particularly preferred according to the invention are characterized in that $R^4$=the acyl radical of a natural fatty acid selected from caprylic acid, capric acid and lauric acid, in particular mixtures thereof, and coconut fatty acid mixtures, and $R^5$ is selected from sulphosuccinic acid radicals of the formula IIa or IIb.

The present invention further provides a process for the preparation of sulphosuccinates based on polyglycerol partial esters, comprising the process steps:

A) reaction of polyglycerol having a degree of polymerization of 2-16 with 20-80 mol per cent, preferably with 30 to 60 mol per cent, based on the polyglycerol, of one or more saturated or partially unsaturated carboxylic acids containing 6-22 carbon atoms which may be substituted by hydroxyl groups, preferably a carboxylic acid having 8-18 carbon atoms, in particular with a caprylic acid, capric acid or lauric acid, in particular mixtures thereof, or coconut fatty acid mixtures, B) selected from at least one of the process steps B1) reaction with 30-600, preferably 50-500, in particular 70-300 mol per cent of maleic anhydride and/or itaconic anhydride, based on the polyglycerol, and B2) reaction with 30-600, preferably 50-500, in particular 70-300 mol per cent of itaconic acid, based on the polyglycerol, C) sulphonation with alkali metal, alkaline earth metal and/or ammonium sulphite salts such as sodium sulphite or sodium hydrogensulphite or sodium disulphite and optionally D) purification of the sulphosuccinates based on polyglycerol partial esters.

Since the process according to the invention is intended to provide—apart from the polyether structures present on the basis of the polyglycerol—polyglycol ether-free sulphosuccinates, further process steps are excluded in the process according to the invention which could lead to further polyether structures; such excluded process steps are in particular alkoxylations, such as ethoxylations (with ethylene oxide) or propoxylations (with propylene oxide).

Process step A) is preferably carried out as described in G. Jakobson, *Fette, Seifen, Anstrichmittel* 1986, 88, 101-105. In particular, according to the invention, in process step A), the polyglycerol is esterified with the carboxylic acid or acids, optionally with co-use of an esterification catalyst, at 150-250° C. while removing the water of reaction.

Process steps B) and C) are preferably carried out as described in DE-A 27 00 072. Here, in B 1), stirring is carried out at 60-80° C. until the anhydride has completely reacted. Process step B2) is carried out with itaconic acid at a temperature of 120-250° C., it being possible to also combine this process step B2) with process step A as a one-pot synthesis. In process step C), the maleic acid ester and/or the itaconic acid ester is added to an aqueous sodium sulphite solution or sodium hydrogensulphite solution or sodium disulphite solution and sulphonated at 60-90° C. until the sulphite has completely reacted.

Optionally, the aqueous product is rendered pH-neutral.

Processes preferred according to the invention are characterized in that, in process step A), the polyglycerol is reacted with 10-50 per cent by weight, preferably with 15-40 per cent by weight, based on the polyglycerol, of at least one carboxylic acid.

Processes preferred according to the invention are characterized in that, in process step A), the polyglycerol has an average degree of polymerization n of 2-11, particularly preferably of 3-8, it being possible to determine this as described above.

In process step A), preference is given to using natural fatty acids having 8-18 carbon atoms, in particular fatty acids selected from oenanthic acid, caprylic acid, pelargonic acid, capric acid, lauric acid, myristic acid, pentadecanoic acid, palmitic acid, margaric acid, stearic acid, undecylenic acid, myristoleic acid, palmitoleic acid, petroselic acid, oleic acid, elaidic acid, vaccenic acid, linoleic acid, α-linolenic acid, γ-linolenic acid, calendic acid, punicic acid, α-elaeostearic acid and β-elaeostearic acid, where caprylic acid, capric acid and lauric acid, in particular mixtures thereof, and coconut fatty acids are particularly preferred.

In process step B), preference is given to using maleic anhydride according to B1).

In an alternative embodiment of the process according to the invention, in process step B), preference is given to using itaconic anhydride according to B1) or itaconic acid according to B2).

Processes particularly preferred according to the invention use, in process step A), at least one carboxylic acid selected from caprylic acid, capric acid and lauric acid, in particular mixtures thereof, and coconut fatty acid mixtures and, in process step B), maleic anhydride according to B1).

It is preferred according to the invention that, at the end of process step C), an aqueous solution with a dry content of at least 40% by weight, in particular at least 55% by weight, based on the total reaction mixture, is present which can be controlled through choice of the water content in process step C).

If required, in the course of process step D), further water can be distilled off. In particular, the water can be removed here to the extent that an anhydrous powder is obtained.

This can also be achieved by other drying methods such as, for example, spray-drying.

This powder can advantageously be stored and likewise advantageously be used in solid end products such as, for example, syndet soaps.

The present invention further provides polyglycerol partial ester-based sulphosuccinates obtainable by the process according to the invention, particular preference being given according to the invention to sulphosuccinates which are obtainable by processes preferred according to the invention.

The sulphosuccinates of the present invention can advantageously be used for producing care and cleaning formulations, in particular for skin and skin appendages, such as, for example, liquid soaps, shower gels or shampoos, and also care and cleaning formulations for the home and industry, these preferably being selected from the group of cosmetic, cleaning and care formulations. Uses of this type are therefore likewise provided by the present invention.

The term "care formulation" is understood here as meaning a formulation which satisfies the purpose of restoring an object to its original form, of reducing or avoiding the effects of external influences (e.g., time, light, temperature, pressure, soiling, chemical reactions with other reactive compounds that come into contact with the object) such as, for example, ageing, soiling, material fatigue, bleaching, or even of improving desired positive properties of the object. For the last point, mention may be made for example of the shine of the object under consideration.

In this connection, care and cleaning formulations are not limited to cosmetic, pharmaceutical or dermatological formulations such as e.g., for the treatment of the skin and the hair in the form of shower gels, foam baths, liquid soaps, hair shampoos, 2-in-1 shampoos, hair rinses, permanent wave fixing solutions, hair coloring shampoos, hair setting compositions, hair treatments, hair arranging compositions, hairstyling compositions, blow-drying lotions, setting foams, hair treatments, leave-in conditions, hair smoothing compositions, shine improving compositions and compositions for coloring the hair, and also other cleaning and care formulations, but can also be those formulations as used in the home and industry, for example for the care and cleaning of surfaces of inanimate objects such as, for example tiles, wood, glass, ceramic, linoleum, plastic, painted surfaces, leather, materials, fibres. Examples of such objects are window panes and sills, shower screens, floors such as carpets, tiles, laminates, parquet, cork floorings, marble, stone and fine stoneware floors, household ceramics such as WCs, washbasins, bidets, shower trays, bath tubs, door handles, fittings, domestic appliances such as washing machines, tumble dryers, dishwashers, sinks made of ceramic or stainless steel, furniture such as tables, chairs, benches, work surfaces, windows, cooking utensils, crockery and cutlery, laundry, in particular laundry worn close to the body ("underwear"), watercraft, vehicles and aircraft such as cars, buses, motorboats and sailboats, tools such as surgical instruments, vacuum cleaners, engines, pipelines, tanks and appliances for transportation, processing and storage in food processing. Consequently, in this connection, the use is in cleaning and care compositions for the home, industry and institutions.

In this connection, the surface to be cared for and cleaned is preferably cooking utensils and domestic appliances.

The present invention also further provides the care and cleaning formulations, in particular for skin and skin appendages, and also for the home and industry, in particular cosmetic formulations, these preferably being selected from the group of the skin and hair treatment compositions, for example shampoos with or without marked conditioning effect, liquid soaps and shower gels, comprising sulphosuccinates according to the invention.

A formulation preferred according to the invention comprises the sulphosuccinates according to the invention in an amount of from of 0.1% by weight to 99% by weight, preferably in an amount of from 0.5% by weight to 20% by weight, particularly preferably in an amount of from 1.0% by weight to 10% by weight, the % by weight referring to the total formulation.

Cosmetic care and cleaning formulations according to the invention can, for example, comprise at least one additional component selected from the group of
emollients,
emulsifiers,
thickeners/viscosity regulators/stabilizers,
antioxidants,
hydrotropes (or polyols),
solids and fillers,
pearlescent additives,
deodorant and antiperspirant active ingredients,
insect repellents,
self-tanning agents,
preservatives,
conditioners,
perfumes,
dyes,
cosmetic active ingredients,
care additives,
superfatting agents,
solvents.

Substances which can be used as exemplary representatives of the individual groups are known to the person skilled in the art and can be found, for example, in EP2273966A1. This patent application is hereby incorporated by reference and thus forms part of the disclosure.

As regards further optional components and the employed amounts of these components, reference is made expressly to the relevant handbooks known to the person skilled in the art, for example K. Schrader, "Grundlagen und Rezepturen der Kosmetika" [Fundamentals and formulations of cosmetics], 2nd edition, pages 329 to 341, Hüthig Buch Verlag Heidelberg.

The amounts of the particular additives are determined by the intended use.

Typical guide formulations for the particular applications are known prior art and are contained, for example, in the brochures of the manufacturers of the particular basic materials and active ingredients. These existing formulations can generally be adopted unchanged. If required, for the purposes of adaptation and optimization, the desired modifications, however, can be undertaken without complication by means of simple experiments.

Preferred formulations according to the invention are aqueous, surface-active formulations; these comprise at least 50% by weight, preferably 70% by weight, of water and, as well as the sulphosuccinates according to the invention, at least one further surfactant.

In the formulations according to the invention, as well as the sulphosuccinates according to the invention, in particular nonionic surfactants of the component selected from the group consisting of glycerol mono- and diesters and sorbitan mono- and diesters of saturated and unsaturated fatty acids, alkyl mono- and oligoglycosides, partial esters based on linear, branched, unsaturated or saturated fatty acids, ricinoleic acid, and 12-hydroxystearic acid and glycerol, polyglycerol, pentaerythritol, dipentaerythritol, sugar alcohols (e.g., sorbitol), alkyl glucosides (e.g., methyl glucoside, butyl glucoside, lauryl glucoside, cocoglucoside), and polyglucosides (e.g., cellulose), mono-, di- and trialkyl phosphates and salts thereof, citric acid esters such as e.g., glyceryl stearate citrate, glyceryl oleate citrate and dilauryl citrate, and glyceryl caprylate, polyglyceryl caprylate, polyglyceryl caprate and mixtures of these surfactants, are present.

In particular, preference is given to cosmetic care and cleaning formulations which are essentially polyglycol ether-free and essentially free from alkoxylated compounds. The term "essentially free from alkoxylated compounds" and "essentially polyglycol ether-free" in connection with the present invention is to be understood as meaning that the formulations have no noteworthy amounts of alkoxylated or polyglycol ether-containing compounds which exert a surface-active effect. In particular, this is to be understood as meaning that these compounds are present in amounts of less than 1% by weight, preferably of less than 0.1% by weight, particularly preferably of less than 0.01% by weight, based on the total formulation, in particular no detectable amounts.

In particular, preference is given to cosmetic care and cleaning formulations which are essentially sulphate-free.

In connection with the present invention, the term "essentially sulphate-free" is to be understood as meaning that the formulations have no noteworthy amounts of sulphated organic compounds which exert a surface-active effect. In particular, this is to be understood as meaning that sulphated organic compounds are present in amounts of less than 1% by weight, preferably of less than 0.1% by weight, particularly preferably of less than 0.01% by weight, based on the total formulation, in particular no detectable amounts. Examples of sulphate-containing surfactants are Sodium Laureth Sulphate, Sodium Lauryl Sulphate, Ammonium Laureth Sulphate, Ammonium Lauryl Sulphate, Sodium Myreth Sulphate, Sodium Coco Sulphate, Sodium Trideceth Sulphate or MIPA-Laureth Sulphate.

Very particularly preferred cosmetic care and cleaning formulations are essentially sulphate-free and essentially polyglycol ether-free and essentially free from alkoxylated compounds.

Preferred cleaning and care formulations according to the invention for the home and industry are textile-softening formulations and textile-care washing and cleaning compositions, dishwashing detergents, household cleaners, disinfectants, disinfectant cleaners, foam cleaners, floor cleaners, carpet cleaners, upholstery cleaners, floor care products, marble cleaners, parquet cleaners, stone and ceramic floor cleaners, wipe care compositions, stainless steel cleaners, glass cleaners, dishwashing detergents, plastic cleaners, sanitary cleaners, wood cleaners, leather cleaners, laundry detergents, laundry care compositions, disinfectant washing compositions, standard detergents, gentle detergents, wool detergents, fabric softeners and impregnation compositions, particular preference being given to dishwashing detergents and household cleaning compositions, in particular hand dishwashing detergents.

Particularly preferred cleaning and care formulations according to the invention for the home and industry additionally comprise one or more substances from the group of the surfactants, builders, bleaches, bleach activators, enzymes, perfumes, perfume carriers, fluorescent agents, dyes, foam inhibitors, silicone oils, antiredeposition agents, optical brighteners, greying inhibitors, shrink preventers, anticrease agents, color transfer inhibitors, antimicrobial active ingredients, germicides, fungicides, antioxidants, preservatives, corrosion inhibitors, antistats, bittering agents, ironing aids, phobicizing and impregnation agents, swelling and slip-resist agents, neutral filling salts, and UV absorbers.

In particular, the cleaning and cleaning and care formulations according to the invention for the home and industry can comprise between 0.001 and 90% by weight, particularly preferably 0.01 to 45% by weight, of one or more of the further ingredients specified here, the % by weight referring to the overall formulation.

Examples of surfactants which can be used are described in WO 2007/115872, page 17, line 28 to page 21, line 24.

Examples of builder substances, builders, bleaches, bleach activators, bleach catalysts and enzymes are described in WO 2007/115872, page 22, line 7 to page 25, line 26.

Antiredeposition agents, optical brighteners, greying inhibitors, color transfer inhibitors are described by way of example in WO 2007/115872 on page 26, line 15 to page 28, line 2.

Examples of anticrease agents, antimicrobial active ingredients, germicides, fungicides, antioxidants, preservatives, antistats, ironing aids, and UV absorbers are described in WO 2007/115872 on page 28, line 14 to page 30, line 22. Their explicit disclosure in this respect forms part of this disclosure by virtue of this reference.

Another field of use in which the sulphosuccinates according to the invention can advantageously be used is crop protection since the sulphosuccinates according to the invention function therein as adjuvant such as, for example, as a wetting agent. The present invention therefore further provides the use of the sulphosuccinates according to the invention for producing crop protection formulations, the use of the sulphosuccinates according to the invention as adjuvant for agrochemical applications, and also as formulation additive of pesticide formulations.

In this connection, the presence of the sulphosuccinates according to the invention advantageously reduces the required amount of active ingredients.

Consequently, the present invention further provides a crop protection formulation which comprises the sulphosuccinates according to the invention. Preferred crop protection formulations comprise at least one pesticide as well as the sulphosuccinates according to the invention.

The sulphosuccinates according to the invention and also the crop protection formulations comprising the sulphosuccinates according to the invention can advantageously be used for the surface treatment of green areas, such as, for example, golf courses, of peat, fertilizers and the like.

The examples listed below describe the present invention by way of example without intending to limit the invention, the scope of application of which arises from the entire description and the claims, to the embodiments specified in the examples.

EXAMPLES

1. Synthesis of polyglycerol partial esters as raw materials for the sulphosuccinate syntheses:

1.1. Synthesis of polyglyceryl caprylate/caprate A:

While introducing nitrogen, 280 g of polyglycerol (hydroxyl number=1104 mg KOH/g) and 70.0 g of caprylic/capric acid (acid number=361 mg KOH/g) were stirred at 240° C. until an acid number of 0.5 mg KOH/g was reached. The water formed in the course of the reaction was distilled off continuously. After cooling to room temperature, the reaction product was in the form of a clear liquid.

1.2. Synthesis of polyglyceryl caprylate/caprate B:

While introducing nitrogen, 144 g of polyglycerol (hydroxyl number 32 1113 mg KOH/g) and 36.0 g caprylic/capric acid (acid number=355 mg KOH/g) was stirred at 210° C. until an acid number of 1.0 mg KOH/g was reached. The water formed in the course of the reaction was distilled off continuously. After cooling to room temperature, the reaction product was in the form of a clear liquid.

1.3. Synthesis of polyglyceryl caprate:

While introducing nitrogen, 969 g of polyglycerol (hydroxyl number=1020 mg KOH/g) and 236 g of capric acid was stirred at 240° C. until an acid number of 0.9 mg KOH/g was reached. The water formed in the course of the reaction was distilled off continuously. After cooling to room temperature, the reaction product was in the form of a clear liquid.

1.4. Synthesis of polyglyceryl cocoate A:

While introducing nitrogen, 137 g of polyglycerol (hydroxyl number=930 mg KOH/g) and 24.2 g of refined coconut fatty acid (C8-C18; acid number=270 mg KOH/g) were stirred at 230° C. until an acid number of 0.7 mg KOH/g was reached. The water formed in the course of the reaction was distilled off continuously. After cooling to room temperature, the reaction product was in the form of a clear liquid.

1.5. Synthesis of polyglyceryl laurate:

While introducing nitrogen, 130 g of polyglycerol (hydroxyl number=960 mg KOH/g) and 22.9 g of lauric acid were stirred at 240° C. until an acid number of 0.9 mg KOH/g was reached. The water formed in the course of the reaction was distilled off continuously. After cooling to room temperature, the reaction product was in the form of a clear liquid.

1.6. Synthesis of polyglyceryl cocoate B:

The synthesis was carried out according to Example 1.1 from EP0794173 by reacting 229 g of polyglycerol (hydroxyl number=1104 mg KOH/g) with 210 g of hydrogenated coconut fatty acid (C12-C18; acid number=257 mg KOH/g). After cooling to room temperature, the reaction product was in the form of a cloudy liquid and had an acid number of 2.0 mg KOH/g.

1.7. Synthesis of polyglyceryl cocoate C:

The synthesis was carried out according to Example 1.4 from EP0794173 by reacting 87.0 g of polyglycerol-T (Solvay; hydroxyl number=1060 mg KOH/g) with 82.7 g of refined coconut fatty acid (C8-C18; acid number=270 mg KOH/g). After cooling to room temperature, the reaction product was in the form of a cloudy liquid and had an acid number of 0.3 mg KOH/g.

2. Sulphosuccinate syntheses:

2.1. Sulphosuccinate 1 (According to the Invention):

According to EP0794173 (Examples 3.3-3.6), 135 g of polyglyceryl caprylate/caprate A from Example 1.1 were reacted with 45.1 g of maleic anhydride and then 94.4 g of the resulting maleic acid ester were sulphonated with a solution of 22.3 g of sodium disulphite in 70.0 g of water. After adjusting the pH to 6.5-7 with sodium hydroxide solution, the reaction product was obtained as a low viscosity, clear, 60% strength aqueous solution which was evidently storage-stable for at least 8 weeks at temperatures between 5 and 50° C. and, after 5 freeze-thaw cycles (freezing to −15° C. and allowing to thaw again), was externally unchanged, clear and homogeneous.

2.2. Sulphosuccinate2 (According to the Invention):

In accordance with EP0794173 (Examples 3.3-3.6), 100 g of polyglyceryl caprylate/caprate B from Example 1.2 were reacted with 30.6 g of maleic anhydride and then 90.7 g of the resulting maleic acid ester were sulphonated with a solution of 20.6 g of sodium disulphite in 67.0 g of water. After adjusting the pH to 6.5-7 with sodium hydroxide solution, the reaction product was obtained as a low viscosity, clear, 60% strength aqueous solution which was evidently storage-stable for at least 8 weeks at temperatures between 5 and 50° C. and, after 5 freeze-thaw cycles (freezing to −15° C. and allowing to thaw again), was externally unchanged, clear and homogeneous.

2.3. Sulphosuccinate 3 (According to the Invention):

According to EP0794173 (Examples 3.3-3.6), 423 g of polyglyceryl caprate from Example 1.3 were reacted with 98.1 g of maleic anhydride and then 450 g of the maleic acid ester obtained were sulphonated with a solution of 82.3 g of sodium disulphite in 337 g of water. After adjusting the pH to 6.5-7 with sodium hydroxide solution, the reaction product was obtained as a low viscosity, clear, 60% strength aqueous solution which was evidently storage-stable for at least 8 weeks at temperatures between 5 and 50° C. and, after 5 freeze-thaw cycles (freezing to −15° C. and allowing to thaw again), was externally unchanged, clear and homogeneous.

2.4. Sulphosuccinate 4 (According to the Invention):

In accordance with EP0794173 (Examples 3.3-3.6), 342 g of polyglyceryl caprate from Example 1.3 were reacted with 158 g of maleic anhydride and then 170 g of the resulting maleic acid ester were sulphonated with a solution of 52.2 g of sodium disulphite in 136 g of water. After adjusting the pH to 6.5-7 with sodium hydroxide solution, the reaction mixture was obtained as a low viscosity, clear, 60% strength aqueous solution which was evidently storage-stable for at least 8 weeks at temperatures between 5 and 50° C. and, after 5 freeze-thaw cycles (freezing to −15° C. and allowing to thaw again), was externally unchanged, clear and homogeneous.

2.5. Sulphosuccinate 5 (According to the Invention):

In accordance with EP0794173 (Examples 3.3-3.6), 295 g of polyglyceryl caprate from Example 1.3 were reacted with 205 g of maleic anhydride and then 150 g of the resulting maleic acid ester were sulphated with a solution of 59.6 g of sodium disulphite in 127 g of water. After adjusting the pH to 6.5-7 with sodium hydroxide solution, the reaction product was obtained as a low viscosity, clear, 60% strength aqueous solution which was evidently storage-stable for at least 8 weeks at temperatures between 5 and 50° C. and, after 5 freeze-thaw cycles (freezing to −15° C. and allowing to thaw again), was externally unchanged, clear and homogeneous.

2.6. Sulphosuccinate 6 (According to the Invention):

In accordance with EP0794173 (Examples 3.3-3.6), 156 g of polyglyceryl cocoate A from Example 1.4 were reacted with 28.9 g of maleic anhydride and then 103.8 g of the resulting maleic acid ester were sulphonated with a solution of 15.6 g of sodium disulphite in 74.2 g of water. After adjusting the pH to 6.5-7 with sodium hydroxide solution, the reaction product was obtained as a low viscosity, clear, 60% strength aqueous solution which was evidently storage-stable for at least 8 weeks at temperatures between 5 and 50° C. and, after 5 freeze-thaw cycles (freezing to −15° C. and allowing to thaw again), was externally unchanged, clear and homogeneous.

2.7. Sulphosuccinate 7 (According to the Invention):

In accordance with EP0794173 (Examples 3.3-3.6), 150 g of polyglyceryl laurate from Example 1.5 were reacted with 27.4 g of maleic anhydride and then 75.4 g of the resulting maleic acid ester were sulphonated with a solution of 11.3 g of sodium disulphite in 75.4 g of water. After adjusting the pH to 6.5-7 with sodium hydroxide solution, the reaction product was obtained as low viscosity, clear, 60% strength aqueous solution which was evidently storage-stable for at least 8 weeks at temperatures between 5 and 50° C. and, after 5 freeze-thaw cycles (freezing to −15° C. and allowing to thaw again), was externally unchanged, clear and homogeneous.

2.8. Sulphosuccinate 8 (not According to the Invention):

In accordance with Example 3.4 from EP0794173, 156 g of polyglyceryl cocoate B from Example 1.6 were reacted with 44.5 g of maleic anhydride and then 67.2 g of the resulting maleic acid ester were sulphonated with a solution of 14.8 g of sodium disulphite in 122 g of water. The pH was adjusted with sodium hydroxide solution. The reaction product was obtained as a cloudy, 40% strength aqueous suspension and separated into 2 phases after 2 days at room temperature.

2.9. Sulphosuccinate 9 (not According to the Invention):

In accordance with Example 3.5 from EP0794173, 79.1 g of polyglyceryl cocoate C from Example 1.7 were reacted with 23.3 g of maleic anhydride and then 60.0 g of the resulting maleic acid ester were sulphonated with a solution of 13.5 g of sodium disulphite in 109 g of water. The pH was adjusted with sodium hydroxide solution. The reaction product was obtained as a cloudy, 40% strength aqueous suspension and separated into 2 phases after 2 days at room temperature.

2.10. Sulphosuccinate 10 (not According to the Invention):

Polyglycol ether-containing sulphosuccinate REWOPOL® SB FA 30 B (commercially available from Evonik Industries AG, INCI: Disodium Laureth Sulphosuccinate). The product consists of 40% sulphosuccinate active ingredient.

2.11. Sulphomethylsuccinate 11 (According to the Invention):

In accordance with EP0794173 (Examples 3.3-3.6), 164 g of polyglyceryl caprylate/caprate B from Example 1.2 were reacted with 66.0 g of itaconic anhydride and then 94.9 g of the resulting itaconic acid ester were sulphonated with a solution of 21.9 g of sodium disulphite in 70.2 g of water. After adjusting the pH to 6.5-7 with sodium hydroxide solution, the reaction product was obtained as low viscosity, clear, 60% strength aqueous solution which was evidently storage-stable for at least 8 weeks at 20° C.

2.12. Sulphomethylsuccinate 12 (According to the Invention):

In accordance with EP0794173 (Examples 3.3-3.6), 172 g of polyglycerylcaprate from Example 1.3 were reacted with 48.0 g of itaconic anhydride and then 102 g of the resulting itaconic acid ester were sulphonated with a solution of 17.7 g of sodium disulphite in 72.8 g of water. After adjusting the pH to 6.5-7 with sodium hydroxide solution, the reaction product was obtained as low viscosity, clear, 60% strength aqueous solution which was evidently storage-stable for at least 8 weeks at 20° C.

TABLE 0

Surface tension (ST) and RBC test of selected products.

|  | ST at c = 1 g/l [mN/m] | RBC test [L/D value] |
|---|---|---|
| Sulphosuccinate 1 | 25.4 | >100 |
| Sulphosuccinate 3 | 25.4 | >100 |
| Sulphosuccinate 6 | 31.4 | >100 |
| Example 3.4 from EP0794173 | 34.8 | >100 |
| Example 3.5 from EP0794173 | 38.4 | >100 |

Analysis methods:
Surface tension:
  measured using Krüss tensiometer K100 at c=1 g/l in deionized water.
Skin compatibility:
  RBC test, see W. J. W. Pape, U. Pfannenbecker, U. Hoppe, Mol. Toxicol. 1987, 1, 525.

Evaluation:

| L/D value | Classification |
|---|---|
| >100 | Non-irritative |
| >10 | Slightly irritative |
| >1 | Moderately irritative |
| >0.1 | Irritative |
| <0.1 | Highly irritative |

Viscosities:
  Measured using a Brookfield rotary viscometer (beaker and spindle) at 25° C. in accordance with the instructions of the instrument manufacturer.

Application Properties:
Application area Cosmetics:
  Hereinbelow, the products described above were tested in cosmetic formulations.
  The formulation constituents are named in the compositions in the form of the generally recognized INCI nomenclature. All concentrations are given in per cent by weight in the application examples.

Testing the skin care capacity and the foam properties in surfactant mixtures using a hand-washing test:
  To evaluate the skin care capacity and the foam properties of the sulphosuccinates 1, 3 and 6 according to the invention and also of the sulphomethylsuccinate 11 in aqueous, surface-active formulations, sensory hand washing tests were carried out compared to the comparative examples sulphosuccinate 8 or 9 and 10 according to the prior art. Comparative Example 10 is widespread in the industry as a mild sulphosuccinate and serves as a mild and universally useful surfactant for aqueous formulations.
  A group consisting of 10 trained subjects washed their hands in a defined way and evaluated foam properties and skin feel using a grading scale from 1 (poor) to 5 (very good).
  The products used were tested in each case in a standardized surfactant formulation. In a first test, a test formulation with the standard surfactant system 9% active sodium laureth sulphate and 3% active sulphosuccinate secondary surfactant was used (Table 1).

TABLE 1

Test formulations for hand washing test I:

| Formulation Examples | 1a | 3a | 6a | 11a | C8a | C10a |
|---|---|---|---|---|---|---|
| Texapon ® NSO, BASF Cognis, 28% strength, (INCI: Sodium Laureth Sulphate) | 32.0% | 32.0% | 32.0% | 32.0% | 32.0% | 32.0% |
| NaCl | 3.0% | 3.0% | 3.0% | 3.0% | 3.0% | 3.0% |
| Water, demineralized | 60.0% | 60.0% | 60.0% | 60.0% | 57.5% | 57.5% |

TABLE 1-continued

Test formulations for hand washing test I:

| Formulation Examples | 1a | 3a | 6a | 11a | C8a | C10a |
|---|---|---|---|---|---|---|
| Sulphosuccinate Example 1, 60% strength (according to the invention) | 5.0% | | | | | |
| Sulphosuccinate Example 3, 60% strength (according to the invention) | | 5.0% | | | | |
| Sulphosuccinate Example 6, 60% strength (according to the invention) | | | 5.0% | | | |
| Sulphomethylsuccinate Example 11, 60% strength (according to the invention) | | | | 5.0% | | |
| Sulphosuccinate Example 8, 40% strength (not according to the invention) | | | | | 7.5% | |
| Comparative Example 10, 40% strength (not according to the invention) | | | | | | 7.5% |

The sensory test results are summarized in Table 2.

TABLE 2

Results of the hand washing test I:

| Test Formulation | 1a | 3a | 6a | 11a | C8a | C10a |
|---|---|---|---|---|---|---|
| Foaming behaviour | 3.2 | 3.4 | 3.3 | 3.2 | 3.1 | 3.0 |
| Foam volume | 2.9 | 3.1 | 3.2 | 2.9 | 2.9 | 2.9 |
| Foam creaminess | 2.9 | 2.9 | 2.9 | 2.9 | 2.8 | 2.9 |
| Skin feel during washing | 3.3 | 3.3 | 3.2 | 3.2 | 3.0 | 3.2 |
| Skin smoothness | 2.6 | 2.4 | 2.7 | 2.7 | 2.3 | 2.2 |
| Skin softness | 2.7 | 2.9 | 2.4 | 2.7 | 2.4 | 2.5 |
| Skin smoothness after 3 min | 3.5 | 3.4 | 3.4 | 3.5 | 3.2 | 3.3 |
| Skin softness after 3 min | 3.4 | 3.3 | 3.3 | 3.4 | 3.1 | 3.2 |

Table 2 shows the results of the hand washing test I. It is clear from the measurement results that the formulations 1a, 2a, 3a and 11a according to the invention using the sulphosuccinates 1, 3 and 6 according to the invention and also the sulphomethylsuccinate 11 were surprisingly superior or at least equivalent in virtually all application properties compared to the comparison formulation C10a according to the prior art and also compared to the formulation with sulphosuccinate Example 8.

Against this background, the results of the formulations 1a, 3a, 6a and 11a according to the invention are to be termed very good and display a considerable improvement over the prior art.

It is clear from the measurement values that the sulphosuccinate 1 according to the invention in the formulation 1a and the sulphomethylsuccinate 11 according to the invention in formulation 11a led to a significant improvement specifically in the case of skin smoothness directly after washing. Furthermore, the measurement values revealed that the sulphosuccinate 3 according to the invention in the formulation 3a has shown significantly better values for the foaming behaviour and the skin softness directly after washing. The sulphosuccinate 6 according to the invention in the formulation 6a exhibited a clear improvement in the case of the foaming behaviour, foam volume and skin smoothness after washing.

As well as the standard test formulation from Table 1, a formulation with additives of only polyglycol ether-free cosurfactants was also investigated. A formulation with 4.8% active sodium cocoamphoacetate, 4.9% active cocamidopropyl betaine and 3.6% active sulphosuccinate was tested (Table 3).

TABLE 3

Test formulations for hand washing test II:

| Formulation Examples | 1b | 3b | 6b | C9b | C10b |
|---|---|---|---|---|---|
| TEGO ® Betain F 50, Evonik Industries AG, 38% strength, (INCI: Cocamidopropyl Betaine) | 12.9% | 12.9% | 12.9% | 12.9% | 12.9% |
| REWOTERIC ® AM C, Evonik Industries AG, 32% strength, (INCI: Sodium Cocoamphoacetate) | 15.0% | 15.0% | 15.0% | 15.0% | 15.0% |
| NaCl | 3.0% | 3.0% | 3.0% | 3.0% | 3.0% |
| Water, demineralized | 63.1% | 63.1% | 63.1% | 60.1% | 60.1% |
| Sulphosuccinate Example 1, 60% strength (according to the invention) | 6.0% | | | | |
| Sulphosuccinate Example 3, 60% strength (according to the invention) | | 6.0% | | | |
| Sulphosuccinate Example 6, 60% strength (according to the invention) | | | 6.0% | | |
| Sulphosuccinate Example 9, 40% strength (not according to the invention) | | | | 9.0% | |
| Comparative Example 10, 40% strength (not according to the invention) | | | | | 9.0% |

The sensory test results are summarized in Table 4.

TABLE 4

Results of the hand washing test II:

| Test Formulation | 1b | 3b | 6b | C9b | C10b |
|---|---|---|---|---|---|
| Foaming behaviour | 3.4 | 3.2 | 3.4 | 3.2 | 3.2 |
| Foam volume | 3.6 | 3.4 | 3.4 | 3.4 | 3.4 |
| Foam creaminess | 3.6 | 3.7 | 3.4 | 3.1 | 3.3 |
| Skin feel during washing | 3.8 | 4.0 | 3.8 | 3.7 | 3.8 |
| Skin smoothness | 2.6 | 2.5 | 2.6 | 2.5 | 2.4 |
| Skin softness | 2.8 | 2.8 | 2.8 | 3.0 | 2.9 |
| Skin smoothness after 3 min | 3.6 | 3.4 | 3.6 | 3.4 | 3.3 |
| Skin softness after 3 min | 3.3 | 3.2 | 3.3 | 3.2 | 3.2 |

Table 4 shows the results of the hand washing test II. It is clear from the measurement results that the formulations 1b, 3b and 6b according to the invention using the sulphosuccinates 1, 3 and 6 according to the invention were surprisingly superior or at least equivalent in virtually all application properties (apart from in the case of skin softness directly after washing) compared to the comparison formulation C10b according to the prior art and also compared to the formulation C9b with sulphosuccinate Example 9.

It is clear from the measurement values that the sulphosuccinate 1 according to the invention in the formulation 1b has led to a significant improvement specifically in the case of the foam creaminess and the skin smoothness 3 min after washing. In addition, the measurement values reveal that the sulphosuccinate 3 according to the invention in the formulation 3b has significantly better values in the case of the foam creaminess. The sulphosuccinate 6 according to the invention in the formulation 6b displayed a considerable improvement in the case of skin smoothness after 3 min.

Against this background, the results of the formulations 1b, 3b and 6b according to the invention are deemed to be very good and exhibit an improvement over the prior art.

Testing the Thickening of Surface-Active Formulations:

To evaluate the thickening suitability of formulations with the sulphosuccinates according to the invention, a number of different surfactant solutions were prepared, admixed with different thickeners, and the achieved viscosities of the formulations were measured.

TABLE 5

Test formulations for viscosity measurements I:

| Formulation Examples | 1c | 3c | 6c | C10c |
|---|---|---|---|---|
| Texapon ® NSO, BASF Cognis, 28% strength, (INCI: Sodium Laureth Sulphate) | 32% | 32% | 32% | 32.0% |
| NaCl | 5% | 5% | 5% | 5.0% |
| Water, demineralized | 58% | 58% | 58% | 55.5% |
| Sulphosuccinate Example 1, 60% strength (according to the invention) | 5% | | | |
| Sulphosuccinate Example 3, 60% strength (according to the invention) | | 5% | | |
| Sulphosuccinate Example 6, 60% strength (according to the invention) | | | 5% | |
| Comparative Example 10, 40% strength (not according to the invention) | | | | 7.5% |
| Viscosity (mPa · s) | 3168 | 3072 | 4224 | 2340 |

TABLE 6

Test formulations for viscosity measurements II:

| Formulation examples | 1d | 3d | 6d | C10d |
|---|---|---|---|---|
| Texapon ® NSO, BASF Cognis, 28% strength, (INCI: Sodium Laureth Sulphate) | 32% | 32% | 32% | 32.0% |
| ANTIL ® 120 Plus, Evonik Industries AG, (INCI: PEG-120 Methyl Glucose Dioleate) | 3% | 3% | 3% | 3.0% |
| Water, demineralized | 60% | 60% | 60% | 57.5% |
| Sulphosuccinate Example 1, 60% strength (according to the invention) | 5% | | | |
| Sulphosuccinate Example 3, 60% strength (according to the invention) | | 5% | | |
| Sulphosuccinate Example 6, 60% strength (according to the invention) | | | 5% | |
| Comparative Example 10, 40% strength (not according to the invention) | | | | 7.5% |
| Viscosity (mPa · s) | 6168 | 6072 | 7224 | 5870 |

TABLE 7

Test formulations for viscosity measurements III:

| Formulation Examples | 1e | 3e | 6e | 11e | C10e |
|---|---|---|---|---|---|
| Texapon ® NSO, BASF Cognis, 28% strength, (INCI: Sodium Laureth Sulphate) | 17.9% | 17.9% | 17.9% | 17.9% | 17.9% |

TABLE 7-continued

Test formulations for viscosity measurements III:

| Formulation Examples | 1e | 3e | 6e | 11e | C10e |
|---|---|---|---|---|---|
| TEGO ® Betain F 50, Evonik Industries AG, 38% strength, (INCI: Cocamidopropyl Betaine) | 6.6% | 6.6% | 6.6% | 6.6% | 6.6% |
| ANTIL ® 120 Plus, Evonik Industries AG, (INCI: PEG-120 Methyl Glucose Dioleate) | 0.7% | 0.7% | 0.7% | 0.7% | 0.7% |
| NaCl | 1.0% | 1.0% | 1.0% | 1.0% | 1.0% |
| Water, demineralized | 69.6% | 69.6% | 69.6% | 69.6% | 67.5% |
| Sulphosuccinate Example 1, 60% strength (according to the invention) | 4.2% | | | | |
| Sulphosuccinate Example 3, 60% strength (according to the invention) | | 4.2% | | | |
| Sulphosuccinate Example 6, 60% strength (according to the invention) | | | 4.2% | | |
| Sulphomethylsuccinate Example 11, 60% strength (according to the invention) | | | | 4.2% | |
| Comparative Example 10, 40% strength (not according to the invention) | | | | | 6.3% |
| Viscosity (mPa · s) | 4200 | 4106 | 4650 | 4170 | 1780 |

TABLE 8

Test formulations for viscosity measurements IV:

| Formulation Examples | 1f | 3f | 6f | C8f | C9f | C10f |
|---|---|---|---|---|---|---|
| Texapon ® NSO, BASF Cognis, 28% strength, (INCI: Sodium Laureth Sulphate) | 17.9% | 17.9% | 17.9% | 17.9% | 17.9% | 17.9% |
| TEGO ® Betain F 50, Evonik Industries AG, 38% strength, (INCI: Cocamidopropyl Betaine) | 6.6% | 6.6% | 6.6% | 6.6% | 6.6% | 6.6% |
| REWOMID ® DC 212 S, Evonik Industries AG, (INCI: Cocamide DEA) | 3.8% | 3.8% | 3.8% | 3.8% | 3.8% | 3.8% |
| NaCl | 1.0% | 1.0% | 1.0% | 1.0% | 1.0% | 1.0% |
| Water, demineralized | 66.5% | 66.5% | 66.5% | 64.4% | 64.4% | 64.4% |
| Sulphosuccinate Example 1, 60% strength (according to the invention) | 4.2% | | | | | |
| Sulphosuccinate Example 3, 60% strength (according to the invention) | | 4.2% | | | | |
| Sulphosuccinate Example 6, 60% strength (according to the invention) | | | 4.2% | | | |
| Sulphosuccinate Example 8, 40% strength (not according to the invention) | | | | 6.3% | | |
| Sulphosuccinate Example 9, 40% strength (not according to the invention) | | | | | 6.3% | |
| Comparative Example 10, 40% strength (not according to the invention) | | | | | | 6.3% |
| Viscosity (mPa · s) | 4469 | 3947 | 6005 | 2445 | 2420 | 2320 |

TABLE 9

Test formulations for viscosity measurements V:

| Formulation Examples | 1g | 3g | 6g | C8g | C9g | C10g |
|---|---|---|---|---|---|---|
| Texapon ® LS 35, BASF Cognis, 30% strength, (INCI: Sodium Lauryl Sulphate) | 6.7% | 6.7% | 6.7% | 6.7% | 6.7% | 6.7% |
| TEGO ® Betain F 50, Evonik Industries AG, 38% strength, (INCI: Cocamidopropyl Betaine) | 10.3% | 10.3% | 10.3% | 10.3% | 10.3% | 10.3% |

TABLE 9-continued

Test formulations for viscosity measurements V:

| Formulation Examples | 1g | 3g | 6g | C8g | C9g | C10g |
|---|---|---|---|---|---|---|
| REWOTERIC ® AM C, Evonik Industries AG, 32% strength, (INCI: Sodium Cocoamphoacetate) | 11.9% | 11.9% | 11.9% | 11.9% | 11.9% | 11.9% |
| ANTIL ® SPA 80, Evonik Industries AG, (INCI: Isostearamide MIPA; Glyceryl Laurate) | 0.5% | 0.5% | 0.5% | 0.5% | 0.5% | 0.5% |
| Water, demineralized | 67.3% | 67.3% | 67.3% | 65.6% | 65.6% | 65.6% |
| Sulphosuccinate Example 1, 60% strength (according to the invention) | 3.3% | | | | | |
| Sulphosuccinate Example 3, 60% strength (according to the invention) | | 3.3% | | | | |
| Sulphosuccinate Example 6, 60% strength (according to the invention) | | | 3.3% | | | |
| Sulphosuccinate Example 8, 40% strength (not according to the invention) | | | | 5.0% | | |
| Sulphosuccinate Example 9, 40% strength (not according to the invention) | | | | | 5.0% | |
| Comparative Example 10, 40% strength (not according to the invention) | | | | | | 5.0% |
| Viscosity (mPa · s) | 4320 | 4619 | 4363 | 810 | 452 | 2880 |

Tables 5-9 show that the formulations according to the invention with the sulphosuccinates 1, 3, 6 according to the invention and also the sulphomethylsuccinate 11 have produced significantly higher viscosities compared to the comparison formulations C8-C10 in specific formulations with a very wide variety of thickeners.

Tables 5 and 6 show a standard surfactant system with 9% active Sodium Laureth Sulphate and 3% active sulphosuccinate. Both with sodium chloride and also with the polymeric, hydrophilic thickener PEG-120 Methyl Glucose Dioleate, the formulations according to the invention could be thickened considerably better than the comparison formulation C10a.

In the formulations of Tables 7 and 8, a very mild and low-concentration surfactant system was used. The total amount of washing-active substance was only 10% (5% active Sodium Laureth Sulphate, 2.5% active Cocamidopropyl Betaine and 2.5% active Sulphosuccinate). These formulations too could be thickened significantly better upon the addition of the sulphosuccinates according to the invention than the corresponding comparison formulations with Comparative Example 10. The effect was evident both when using the polymeric, hydrophilic thickener PEG-120 Methyl Glucose Dioleate and also with the hydrophobic thickener Cocamide DEA. Moreover, in Table 8, it becomes clear that here the sulphosuccinates 1, 3 and 6 according to the invention have achieved significantly higher viscosities than the comparative examples sulphosuccinate Example 8 and 9 according to the prior art.

Also in the very mild, polyglycol ether-free surfactant system of Table 9 (2% active Sodium Lauryl Sulphate, 3.8% Sodium Cocoamphoacetate, 3.9% active Cocamidopropylbetaine and 2% active Sulphosuccinate) considerably higher viscosities could be achieved with 0.5% of the hydrophobic thickener ANTIL® SPA 80 (INCI: Isostearamide MIPA; Glyceryl Laurate) than with the Comparative Example 10 according to the prior art. Also the comparative examples sulphosuccinate Example 8 and 9 according to the prior art dropped off in the viscosity to a surprisingly extreme extent in this system.

Further Formulation Examples of Personal Care:

The formulation examples given in the tables below show exemplary representatives of a large number of possible compositions according to the invention.

If the preparation of the formulation requires beforehand the separate preparation or mixture of formulation constituents, this is referred to as multiphase preparation. If a two-phase preparation is required, the two phases are labelled A and B in the stated tables. In the case of three-phase processes, the three phases are labelled A, B and C.

Unless stated otherwise, the data in the following tables are data in % by weight of active substance. If an active content is given, the percentage is the used amount relative to this non-100% strength mixture and not the amount of active substance.

TABLE 10

| Mild, sulphate-free hair and body cleaning composition | |
|---|---|
| Cocamidopropyl Betaine | 4.9% |
| Sodium Cocoamphoacetate | 4.5% |
| Sulphosuccinate Example 1, 60% strength | 6.0% |
| Sucrose Cocoate | 1.5% |
| PEG-120 Methyl Glucose Dioleate | 2.0% |
| Polyquaternium-10 | 0.2% |
| Water | ad 100.0% |
| Parfum, Preservative | q.s. |
| Citric Acid, 30% | ad pH 5.5 |

TABLE 11

| Mild, sulphate-free body cleaning composition | |
|---|---|
| Sodium Cocoamphoacetate | 4.8% |
| Sulphosuccinate Example 2, 60% strength | 6.8% |
| Sorbitan Sesquicaprylate | 0.9% |
| Water | ad 100.0% |
| Cocamidopropyl Betaine | 4.2% |

TABLE 11-continued

Mild, sulphate-free body cleaning composition

| | |
|---|---|
| Citric Acid, 30% | ad pH 5.0 |
| PEG-120 Methyl Glucose Dioleate | 1.4% |
| Parfum, Preservative | q.s. |

TABLE 12

Sulphate-free baby shampoo

| | |
|---|---|
| Sodium Cocoamphoacetate | 3.2% |
| Isostearamide MIPA; Glyceryl Laurate | 1.0% |
| Water | ad 100.0% |
| Sulphosuccinate Example 6, 60% strength | 10.0% |
| Palmitamidopropyltrimonium Chloride | 1.0% |
| PEG-200 Hydrogenated Glyceryl Palmate; PEG-7 Glyceryl Cocoate | 2.6% |
| Citric Acid, 30% | ad pH 5.7 |
| Parfum, Preservative | q.s. |

TABLE 13

Mild, PEG- and sulphate-free hair and body cleaning composition

| | |
|---|---|
| Lauryl Glucoside | 4.4% |
| Cocamidopropyl Betaine | 5.7% |
| Sodium Cocoamphoacetate | 3.6% |
| Sulphosuccinate Example 2, 60% strength | 2.9% |
| Hydroxypropyl Methylcellulose | 0.5% |
| Isostearamide MIPA; Glyceryl Laurate | 1.4% |
| Polyquaternium-7 | 0.5% |
| Water | ad 100.0% |
| Parfum, Preservative | q.s. |
| Citric Acid, 30% | ad pH 5.5 |

TABLE 14

Shower gel

| | |
|---|---|
| Sodium Laureth Sulphate | 4.0% |
| Sulphosuccinate Example 11, 60% strength | 3.0% |
| Sodium Cocoyl Hydrolyzed Wheat Protein Glutamate | 1.5% |
| Water | ad 100.0% |
| Cocamidopropyl Betaine | 3.0% |
| Capryl/Capramidopropyl Betaine | 1.0% |
| Polyquaternium-7 | 0.5% |
| PEG-200 Hydrogenated Glyceryl Palmate (and) PEG-7 Glyceryl Cocoate | 1.8% |
| Parfum | q.s. |
| Preservative | q.s. |

TABLE 15

Shampoo

| | |
|---|---|
| Water | ad 100.0% |
| Cocamidopropyl Betaine | 4.0% |
| Sodium Lauryl Sulphoacetate | 3.0% |
| Sulphosuccinate Example 2, 60% strength | 3.0% |
| Sodium Lauroyl Sarcosinate | 1.0% |
| Glycol Distearate | 0.9% |
| Sodium Chloride | 0.9% |
| Decyl Glucoside | 0.5% |
| Polyquaternium-10 | 0.3% |
| PPG-5-Ceteth-20 | 0.5% |
| Coco-Betaine | 0.5% |
| PEG-55 Propylene Glycol Oleate | 0.4% |
| Propylene Glycol | 0.3% |
| Salicylic Acid | 0.2% |
| Carbomer | 0.3% |
| Sodium Hydroxide | 0.2% |

TABLE 15-continued

Shampoo

| | |
|---|---|
| Citric Acid | ad pH 5.5 |
| Preservative, Parfum, Dyes | q.s. |

TABLE 16

Body cleaning composition, PEG- & sulphate-free

| | |
|---|---|
| Water | ad 100.0% |
| Sodium Cocoamphoacetate | 5.0% |
| Sulphosuccinate Example 6, 60% strength | 2.0% |
| Cocamidopropyl Betaine | 3.0% |
| Cocamidopropyl Betaine (and) Glyceryl Laurate | 1.0% |
| Citric Acid, 30% | ad pH 5.0 |
| Preservative, Parfum | q.s. |

TABLE 17

Washing emulsion for sensitive and problematic skin

| | |
|---|---|
| Water | ad 100.0% |
| Sodium C14-16 Olefin Sulphonate | 4.0% |
| Sodium Laureth Sulphate | 3.0% |
| Sulphosuccinate Example 3, 60% strength | 4.0% |
| Sodium Chloride | 2.0% |
| Laureth-2 | 1.0% |
| Panthenol | 0.5% |
| Glycol Distearate | 0.5% |
| Saccharide Isomerate | 0.2% |
| Allantoin | 0.2% |
| Niacinamide | 0.1% |
| Pyridoxine HCl | 0.1% |
| Glycine | 0.1% |
| Alanine | 0.1% |
| Lysine | 0.1% |
| Biotin | 0.1% |
| Glycerol | 0.5% |
| Sodium Lauroyl Glutamate | 0.5% |
| Sodium Citrate | 0.5% |
| Cocamidopropyl Betaine | 0.5% |
| Sorbitan Laurate | 0.4% |
| PEG-120 Methyl Glucose Dioleate | 0.3% |
| Preservative, Parfum | q.s. |

TABLE 18

Kids shower & shampoo

| | |
|---|---|
| Water | ad 100% |
| Sulphosuccinate Example 3, 60% strength | 6.0% |
| Cocamidopropyl Hydroxysultaine | 2.5% |
| Cocamidopropyl Betaine | 1.5% |
| Caprylyl/Capryl Glucoside | 1.0% |
| PEG-18 Glyceryl Oleate/Cocoate | 0.7% |
| Laureth-2 | 0.5% |
| Sodium Chloride | 0.5% |
| Panthenol | 0.2% |
| Niacinamide | 0.1% |
| Pyridoxan Hydrochloride | 0.1% |
| Polyquaternium-10 | 0.3% |
| Glycerol | 0.3% |
| Inulin | 0.1% |
| Citric Acid | ad pH 5.7 |
| Preservative, Parfum, Dyes | q.s. |

TABLE 19

Mild baby shampoo

| | |
|---|---|
| Water | ad 100% |
| Sulphosuccinate Example 11, 60% strength | 5.5% |
| Isostearamide MIPA (and) Glyceryl Laurate | 1.7% |
| PEG-7 Glyceryl Cocoate | 0.5% |
| Sodium Cocoamphoacetate | 3.0% |
| Palmitamidopropyltrimonium Chloride | 2.3% |
| Citric Acid, 30% | ad pH 6.0 |
| Preservative, Parfum, Dyes | q.s. |

TABLE 20

Mild face cleaning foam

| | |
|---|---|
| Water | ad 100% |
| Sulphosuccinate Example 5, 60% strength | 8.5% |
| Capryl/Capramidopropyl Betaine | 3.0% |
| Polyglyceryl-3 Caprate | 0.5% |
| Creatine | 0.2% |
| Hydroxypropyl Methylcellulose | 0.5% |
| Sodium Lactate (and) Sodium PCA (and) Glycine (and) Fructose (and) Urea (and) Niacinamide (and) Inositol (and) Sodium Benzoate (and) Lactic Acid | 1.0% |
| Preservative, Parfum | q.s. |

TABLE 21 a) and b): Body cleaning compositions

| | | |
|---|---|---|
| Water | ad 100% | ad 100% |
| Sodium Lauryl Sulphate | 9% | 9% |
| Sulphosuccinate Example 1, 60% strength | 5% | 5% |
| PEG-120 Methyl Glucose Dioleate | 3% | |
| Sodium Chloride | | 5% |
| Preservative, Parfum | q.s. | q.s. |

TABLE 22 a) and b): Body cleaning compositions

| | | |
|---|---|---|
| Water | ad 100% | ad 100% |
| Sodium Lauryl Sulphate | 5.0% | 5.0% |
| Cocamidopropyl Betaine | 2.5% | 2.5% |
| Sulphosuccinate Example 3, 60% strength | 4.2% | 4.2% |
| PEG-120 Methyl Glucose Dioleate | 0.7% | |
| Cocamide DEA | | 3.8% |
| Sodium Chloride | 1.0% | 1.0% |
| Preservative, Parfum | q.s. | q.s. |

TABLE 23 a) and b): Mild, PEG-free body cleaning compositions

| | | |
|---|---|---|
| Water | ad 100% | ad 100% |
| Cocamidopropyl Betaine | 3.9% | 3.9% |
| Sodium Cocoamphoacetate | 3.8% | 3.8% |
| Sodium Lauryl Sulphate | 2.0% | 2.0% |
| Sulphosuccinate Example 1, 60% strength | 3.3% | 3.3% |
| Sorbitan Sesquicaprylate | 0.5% | |
| Isostearamide MIPA; Glyceryl Laurate | | 0.5% |
| Citric Acid | ad pH 5.0 | ad pH 5.0 |
| Preservative, Parfum | q.s. | q.s. |

TABLE 24

Mild, PEG- and sulphate-free body cleaning composition

| | |
|---|---|
| Water | ad 100% |
| Cocamidopropyl Betaine | 5.7% |
| Lauryl Glucoside | 4.4% |
| Sodium Cocoamphoacetate | 3.6% |
| Sulphosuccinate Example 3, 60% strength | 2.8% |
| Isostearamide MIPA; Glyceryl Laurate | 1.4% |
| Citric Acid | ad pH 5.0 |
| Preservative, Parfum | q.s. |

TABLE 25

Mild face cleaning gel; PEG- and sulphate-free

| | |
|---|---|
| Water | ad 100% |
| Coco Glucoside | 4.0% |
| Sodium Cocoyl Glutamate, Disodium Cocoyl Glutamate | 4.0% |
| Glycerol | 3.0% |
| Xanthan Gum | 1.5% |
| Sulphosuccinate Example 6, 60% strength | 1.7% |
| Preservative, Parfum | q.s. |

TABLE 26

Mild face cleaning gel; PEG- and sulphate-free, Ecocert-conform

| | |
|---|---|
| Water | ad 100% |
| Sodium Cocoamphoacetate | 3.2% |
| Polyglyceryl-3 Caprate | 3.0% |
| Cocamidopropyl Betaine | 2.3% |
| Capryl/Capramidopropyl Betaine | 2.3% |
| Xanthan Gum | 1.5% |
| Sodium Chloride | 1.5% |
| Coamidopropyl Betaine; Glyceryl Laurate | 1.3% |
| Sulphosuccinate Example 1, 60% strength | 1.7% |
| Sucrose Cocoate | 0.6% |
| Citric Acid | ad pH 5.0 |
| Preservative, Parfum | q.s. |

TABLE 27

Further formulation examples

| | a | b | c | d | e | f | g | h | i | j |
|---|---|---|---|---|---|---|---|---|---|---|
| Water | ad 100% | | | | | | | | | |
| Sulphosuccinate Example 1, 60% strength | 15.0% | 7.0% | 4.0% | 4.5% | 7.0% | 5.5% | 8.0% | 4.0% | 4.5% | 3.0% |
| Disodium Ricinoleamido MEA-Sulphosuccinate | — | 4.0% | 5.0% | — | — | 1.0% | — | | | |
| Sodium Laureth Sulphate | — | — | — | 7.0% | — | — | — | 4.5% | — | — |
| Ammonium Lauryl Sulphate | — | — | — | — | 5.0% | — | — | — | 3.5% | — |
| Cocamidopropyl Betaine | — | — | — | — | — | 6.0% | — | 2.5% | — | 4.5% |
| Sodium Cocoamphoacetate | — | — | 5.0% | — | — | — | — | — | 3.5% | — |

TABLE 27-continued

Further formulation examples

| | a | b | c | d | e | f | g | h | i | j |
|---|---|---|---|---|---|---|---|---|---|---|
| Coco Glucoside | — | — | — | — | — | — | 5.5% | — | — | 2.5% |
| Sorbitol | — | 1.0% | 0.5% | — | — | — | 1.0% | — | — | 0.5% |
| Sucrose Cocoate | 0.5% | — | 1.0% | 1.0% | 1.0% | 0.5% | 0.3% | 1.0% | 1.0% | — |
| Hydroxypropyl Methylcellulose | 0.5% | 0.5% | 0.3% | — | — | 0.3% | 0.5% | — | — | 0.1% |
| Polyglyceryl-4 Caprate | — | — | — | — | — | — | — | 0.5% | — | — |
| Hydroxypropyl Guar Hydroxypropyltrimonium Chloride | 0.2% | 0.2% | 0.2% | 0.3% | 0.2% | 0.2% | 0.2% | 0.2% | 0.2% | 0.2% |
| Dimethicone (and) Dimethiconol | — | — | — | — | — | — | — | 0.3% | — | — |
| Silicone Quaternium-22 | — | — | — | 1.0% | 0.5% | — | — | — | — | — |
| Amodimethicone | — | — | 0.1% | — | — | — | 0.5% | — | — | — |
| PEG-3 Distearate | — | — | 0.5% | — | 0.5% | — | — | 0.5% | — | 0.5% |
| Acrylates/C10-30 Alkyl Acrylate Crosspolymer | 1.0% | — | — | — | 0.5% | — | — | — | 0.5% | — |
| Sodium Hydroxide, 25% | 1.5% | — | — | — | 0.8% | — | — | — | 0.7% | — |
| Cocamide MEA | — | 1.5% | — | — | — | — | — | — | 1.0% | 0.5% |
| Sorbitan Sesquicaprylate | — | 0.5% | — | 0.5% | — | 1.2% | 1.0% | — | — | 1.3% |
| Sodium Chloride | 1.0% | 1.0% | — | 0.5% | 0.3% | 1.5% | — | 2.0% | 1.5% | — |
| PEG-200 Hydrogenated Glyceryl Palmate; PEG-7 Glyceryl Cocoate | — | — | — | 0.4% | — | — | — | 0.6% | — | — |
| Xanthan Gum | — | 0.5% | 1.2% | — | — | — | 1.0% | — | — | 0.5% |
| Zinc Pyrithione | — | — | — | 0.1% | — | — | — | 0.1% | — | — |
| Pentylene Glycol | — | — | — | 0.1% | — | — | 0.4% | — | — | — |
| Panthenol | 0.1% | 0.1% | 0.1% | 0.1% | 0.1% | 0.1% | 0.1% | 0.1% | 0.1% | 0.1% |
| Citric Acid | | | | | ad pH 5.5 | | | | | |
| Preservative, Parfum, Dyes | | | | | q.s. | | | | | |

TABLE 28

Further formulation examples

| | a | b | c | d | e | f | g | h | i | j |
|---|---|---|---|---|---|---|---|---|---|---|
| Water | | | | | ad 100% | | | | | |
| Sulphosuccinate Example 3, 60% strength | 4.0% | 3.0% | 4.5% | 4.5% | 7.0% | 5.5% | 3.0% | 4.0% | 1.5% | 3.0% |
| Sodium Cocoyl Glycinate | 4.0% | — | — | — | — | — | 2.0% | 1.0% | — | — |
| Sodium Laureth Sulphate | — | 5.0% | 7.0% | — | — | — | — | 4.0% | 4.5% | — |
| Undecylenamidopropyl Betaine | — | 3.0% | 4.0% | 5.0% | — | — | — | — | — | — |
| Cocamidopropyl Betaine | 4.0% | 2.0% | — | 4.0% | 4.5% | — | — | 1.5% | 1.0% | 5.5% |
| Lauroyl Sarcosine | — | — | — | — | 3.0% | 2.0% | 2.0% | — | 2.5% | 1.0% |
| Sodium Cocoyl Isethionate | — | — | — | — | — | — | 2.0% | 1.0% | — | 2.5% |
| Coco Glucoside | — | — | — | 1.0% | — | 5.5% | 2.5% | — | 1.0% | — |
| Glycerol | 0.3% | — | 0.5% | 0.3% | — | 1.0% | 1.0% | — | 0.5% | 0.2% |
| Hydroxypropyl Methylcellulose | 0.5% | — | 0.3% | 0.2% | — | — | 0.2% | — | — | — |
| Glyceryl Caprylate | 0.2% | — | 0.1% | — | — | 0.3% | — | — | 0.5% | — |
| Polyglyceryl-4 Caprate | — | — | — | 0.5% | — | — | 0.5% | — | — | — |
| PEG-40 Hydrogenated Castor Oil | — | 0.2% | — | — | — | — | — | — | — | — |
| Diethylhexyl Carbonate | — | — | 0.1% | — | — | — | — | — | — | — |
| Caprylic/Capric Triglyceride | 0.1% | — | — | 0.2% | — | — | — | — | 0.1% | — |
| Dicaprylylether | — | 0.3% | — | — | 0.5% | — | — | — | — | — |
| Polyquaternium-10 | 0.2% | 0.3% | 0.2% | 0.3% | 0.2% | 0.2% | 0.2% | 0.3% | — | 0.2% |
| Bis-PEG/PPG-20/20 Dimethicone | — | 0.1% | — | — | — | — | — | 0.1% | — | — |
| Glycol Distearate | — | 0.5% | 0.3% | 0.5% | — | — | — | 0.3% | — | 0.5% |
| Carbomer | — | — | — | — | 0.5% | — | — | 0.5% | — | — |
| Sodium Hydroxide, 25% | — | — | — | — | 0.8% | — | — | 0.7% | — | — |
| Cocamide MEA | — | — | 0.3% | — | — | — | — | — | 1.0% | 0.5% |
| Sodium Chloride | 1.0% | 1.5% | 0.5% | 0.5% | 0.3% | 0.5% | — | 1.0% | 1.5% | — |
| PEG-120 Methyl Glucose Dioleate | — | 0.3% | 0.8% | — | — | — | — | — | 0.2% | — |
| Xanthan Gum | — | — | 0.5% | — | 1.0% | 0.8% | — | — | — | 0.3% |
| Climbazole | — | 0.1% | — | 0.1% | — | — | — | — | — | — |

TABLE 28-continued

Further formulation examples

| | a | b | c | d | e | f | g | h | i | j |
|---|---|---|---|---|---|---|---|---|---|---|
| Octopirox | — | — | 0.1% | — | — | — | — | 0.1% | — | — |
| Hydrolyzed Wheat Protein | 0.1% | — | 0.1% | — | — | 0.1% | 0.1% | 0.1% | — | 0.1% |
| Panthenol | 0.1% | 0.1% | 0.1% | 0.1% | 0.1% | 0.1% | 0.1% | — | 0.1% | 0.1% |
| Citric Acid | | | | | ad pH 5.5 | | | | | |
| Preservative, Parfum, Dyes | | | | | q.s. | | | | | |

TABLE 29

List of raw materials used:

| INCI name: | Trade name: |
|---|---|
| Thickeners/stabilizers: | |
| Carbomer | TEGO Carbomer 140, Evonik Industries AG, 100% |
| Acrylates/C10-30 Alkyl Acrylate Crosspolymer | TEGO Carbomer 341 ER, Evonik Industries AG, 100% |
| Cocamide DEA | REWOMID DC 212 S, Evonik Industries AG, 100% |
| Cocamide MEA | REWOMID D 212, Evonik Industries AG, 100% |
| Isostearamide MIPA; Glyceryl Laurate | ANTIL SPA 80, Evonik Industries AG, 100% |
| Sorbitan Sesquicaprylate | ANTIL Soft SC, Evonik Industries AG, 100% |
| Sorbitan Laurate | TEGO SML, Evonik Industries AG, 100% |
| PEG-55 Propylene Glycol Oleate | ANTIL 141 liquid, Evonik Industries AG |
| PEG-120 Methyl Glucose Dioleate | ANTIL 120 Plus, Evonik Industries AG, 100% |
| PEG-18 Glyceryl Oleate/Cocoate | ANTIL 171, Evonik Industries AG, 100% |
| PEG-200 Hydrogenated Glyceryl Palmate; PEG-7 Glyceryl Cocoate | REWODERM LI S 80, Evonik Industries AG, 100% |
| Xanthan Gum | Keltrol CG-SFT, CP Kelco, 100% |
| Pearlizing agents: | |
| PEG-3 Distearate | Cutina TS, BASF Cognis, 100% |
| Glycol Distearate | TEGIN G 1100, Evonik Industries AG, 100% |
| Silicone Additives: | |
| Amodimethicone | DC 949, Dow Corning, 100% |
| Dimethicone (and) Dimethiconol | DC 1503. Dow Corning |
| Silicone Quaternium-22 | ABIL T Quat 60, Evonik Industries AG, 65% |
| Bis-PEG/PPG-20/20 Dimethicone | ABIL B 8832, Evonik Industries AG, 100% |
| Care polymers/film formers: | |
| Polyquaternium-7 | Merquat 550, Nalco, 100% |
| Polyquaternium-10 | Polymer JR 400, Amerchol, 100% |
| Hydroxypropyl Guar Hydroxypropyltrimonium Chloride | Jaguar C-162, Rhodia, 100% |
| Active ingredients: | |
| Panthenol | D-Panthenol USP, BASF, 100% |
| Allantoin | Allantoin, DSM |
| Niacinamide | Niacinamide, USP, DSM Nutrional Products, 100% |
| Creatine | TEGO Cosmo C 100, Evonik Industries AG, 100% |
| Sodium Lactate; Sodium PCA; Glycine; Fructose; Urea; Niacinamide; Inositol; Sodium Benzoate; Lactic Acid | LACTIL, Evonik Industries AG, 100% |
| Salicylic Acid | AEC Salicylic Acid, A & E Connock |
| Pyridoxine HCl | Vitamin B6 Hydrochloride, DSM |
| Hydrolyzed Wheat Protein | Gluadin WLM, BASF Cognis |
| Antidandruff active ingredients: | |
| Climbazole | Crinipan AD, Haarmann & Reimer Fragrance GmbH, 100% |
| Octopirox | Octopirox, Clariant |
| Zinc Pyrithione | Zinc-Pyrion NF, WeylChem, 48% |
| Conditioner: | |
| Palmitamidopropyltrimonium Chloride | VARISOFT PATC, Evonik Industries AG, 60% |
| Surfactants: | |
| Cocamidopropyl Betaine | TEGO Betain F 50, Evonik Industries AG, 38% |
| Capryl/Capramidopropyl Betaine | TEGO Betain 810, Evonik Industries AG, 35% |
| Undecylenamidopropyl Betaine | REWOTERIC AM B U 185, Evonik Industries AG, 30% |
| Coco-Betaine | Dehyton AB 30, BASF Cognis, 31% |
| Sodium Cocoamphoacetate | REWOTERIC AM C, Evonik Industries AG, 32% |
| Disodium Ricinoleamido MEA-Sulphosuccinate | REWODERM S 1333, Evonik Industries AG, 40% |
| Sodium Lauryl Sulphoacetate | Lathanol LAL, Stepan |
| Sodium Laureth Sulphate | Texapon NSO, BASF Cognis, 28% or TEXAPON N 70, 70% |
| Sodium Lauryl Sulphate | Texapon LS 35, BASF Cognis, 30% |
| Cocamidopropyl Hydroxysultaine | Mirataine CBS, Rhodia |
| Lauryl Glucoside | Plantacare 1200 UP, BASF Cognis, 50% |
| Decyl Glucoside | Plantacare 2000 UP, BASF Cognis |
| Coco Glucoside | Plantacare 818 UP, BASF Cognis, 51% |
| Caprylyl/Capryl Glucoside | Plantacare 810 UP, BASF Cognis |
| Sodium Cocoyl Glutamate | Plantapon ACG HC, BASF Cognis |
| Sodium Lauroyl Glutamate | Amisoft LS-11, Ajinomoto |
| Disodium Cocoyl Glutamate | Planatpon ACG LC, BASF Cognis |
| Sodium Cocoyl Hydrolyzed Wheat Protein Glutamate | PGFAC-S, BASF Cognis |
| Sodium Cocoyl Glycinate | Hostapon SG, Clariant |
| Sodium C14-16 Olefin Sulphonate | Bioterge AS-40 AOS, Stepan |
| Sodium Lauroyl Sarcosinate | Crodasinic LS 30, Croda, 30% |
| Lauroyl Sarcosine | Crodasinic L, Croda |
| Sodium Cocoyl Isethionate | Hostapon STCI-85 P, Clariant |
| Refatting agents/emollients: | |
| Polyglyceryl-3 Caprate | TEGOSOFT PC 31, Evonik Industries AG, 100% |
| Glyceryl Caprylate | Dermosoft GMCY, Dr. Straetmans |
| Glyceryl Laurate | Imwitor 312, Sasol |
| Diethylhexyl Carbonate | TEGOSOFT DEC, Evonik Industries AG, 100% |
| Caprylic/Capric Triglyceride | TEGOSOFT CT, Evonik Industries AG, 100% |
| PEG-7 Glyceryl Cocoate | TEGOSOFT GC, Evonik Industries AG, 100% |

TABLE 29-continued

List of raw materials used:

| INCI name: | Trade name: |
|---|---|
| Sucrose Cocoate | TEGOSOFT LSE 65 K, Evonik Industries AG, 100% |
| Sorbitol | Sorbitol USP Powder, Lipo |
| Glycerol | Glycerol EP, vegetable, Spiga Nord, 99.7% |
| Dicaprylyl ether | Cetiol OE, BASF Cognis |
| Foam booster: | |
| Hydroxypropyl Methylcellulose | TEGOCEL HPM 50, Evonik Industries AG, 100% |
| Solubilizers: | |
| PEG-40 Hydrogenated Castor Oil | TAGAT CH 40, Evonik Industries AG, 100% |
| Pentylene Glycol | Hydrolite-5 616751, Symrise |
| Laureth-2 | Marlipal 24/20, Sasol |
| Polyglyceryl-4 Caprate | TEGOSOFT PC 41, Evonik Industries AG, 100% |

Application Area Home Care:

The sulphosuccinates according to the invention are generally suitable for use in cleaning compositions for hard surfaces and in particular in hand dishwashing detergents.

In cleaning compositions for hard surfaces, amphoteric surfactants and particularly alkyl ether sulphates contribute primarily to the cleaning effect. The addition of a skin-mild anionic surfactant leads to better foaming behaviour of the overall formulation. Furthermore, the present invention relates to the use of a composition according to the invention for the cleaning of hard surfaces, in particular dishes. As well as dishes, glasses and cutlery, suitable hard surfaces are also all other hard surfaces, in particular made of glass, porcelain, ceramic, polymeric or metallic materials in the home and commercially.

Compared to other sulphosuccinates, the use of the sulphosuccinate according to the invention leads to an increased foaming behaviour. Table 30 shows a comparison with comparison products available on the market in hard water (20° German hardness). Testing was carried out in a discharge foam test with a use amount of 0.02% active content.

TABLE 30

Foam behaviour in the discharge foam test with 0.02% surfactant active content
Surfactant system = 10:4.5:1.5

| Formulation | Start | 30 s | 60 s | 120 s |
|---|---|---|---|---|
| SLES:CAPB:REWOPOL ® SB CS 50 | 21.0 | 18.0 | 17.5 | 17.0 |
| SLES:CAPB:REWOPOL ® SB FA 30 | 20.0 | 17.5 | 16.5 | 16.0 |
| SLES:CAPB:Example 2 according to the invention | 26.0 | 21.5 | 21.0 | 20.0 |
| SLES:CAPB:REWOPOL ® SB C 212 | 20.0 | 18.0 | 17.0 | 16.5 |

SLES: Sodium Laureth Sulphate;
CAPB: Cocamidopropyl Betaine;
REWOPOL ® SB CS 50: Disodium PEG-5 Laurylcitrate Sulphosuccinate (and) Sodium Laureth Sulphate;
REWOPOL ® SB FA 30 B: Disodium Laureth Sulphosuccinate;
REWOPOL ® SB C 212: Disodium Cocamido MEA-Sulphosuccinate.

Formulation Examples for Home Care:

TABLE 31

Skin-friendly dishwashing detergent for manual use

| Texapon ® N70, BASF Cognis, 70% strength, (INCI: Sodium Laureth Sulphate) | 28.5% |

TABLE 31-continued

Skin-friendly dishwashing detergent for manual use

| Sulphosuccinate Example 2, 60% strength | 2.5% |
| TEGO ® Betain F 50, Evonik Industries AG, 38% strength | 11.8% |
| Water | 57.2% |
| Parfum, Preservative | q.s. |

TABLE 32

Mild kitchen cleaner

| Sulphosuccinate Example 3, 60% strength | 2.5% |
| TEGO ® Betain C 60, Evonik Industries AG, 47% strength | 2.2% |
| Trilon ® M, BASF, 40% strength | 0.7% |
| Water | 94.6% |
| Parfum, Preservative | q.s. |

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

The invention claimed is:

1. A polyglycerol partial ester-based sulphosuccinate of general formula I

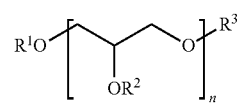

general formula I wherein $R^1$, $R^2$, $R^3$=independently of one another, identical or different H, $R^4$ or $R^5$, $R^4$=a saturated or partially unsaturated acyl radical containing 6-22 carbon atoms which can be substituted by hydroxyl groups, $R^5$ is selected from sulphosuccinic acid radicals of the formula IIa or IIb

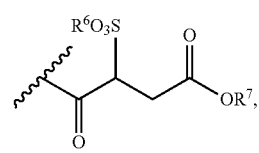

Formula IIa

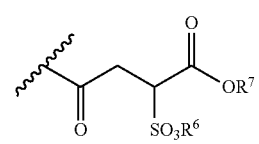

Formula IIb and sulphomethylsuccinic acid radicals of the formula IIc or IId

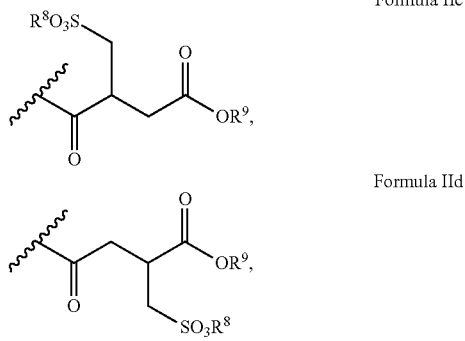

Formula IIc

Formula IId where
R$^6$, R$^7$, R$^8$, R$^9$=independently of one another, identical or different H, an alkali metal or ½ alkaline earth metal or an ammonium group
n=2 to 16,
and wherein
on statistical average, per molecule of the general formula I, 0.2 to 0.8 radicals R$^4$ and
on statistical average, per molecule of the general formula I 0.3 to 6 radicals R$^5$ are present.

2. The sulphosuccinate according to claim 1, wherein R$^1$, R$^2$, R$^3$=H and wherein on statistical average, said sulphosuccinate has a weight ratio of carboxylic acid R$^4$OH to polyglycerol basic backbone of 0.10:1 to 0.50:1.

3. The sulphosuccinate according to claim 1, wherein said sulphosuccinate has an average degree of polymerization n of 2 to 11.

4. The sulphosuccinate according to claim 1, wherein R$^4$=an acyl radical of a fatty acid selected from the group consisting of oenanthic acid, caprylic acid, pelargonic acid, capric acid, lauric acid, myristic acid, pentadecanoic acid, palmitic acid, margaric acid, stearic acid, undecylenic acid, myristoleic acid, palmitoleic acid, petroselic acid, oleic acid, elaidic acid, vaccenic acid, linoleic acid, α-linolenic acid, γ-linolenic acid, calendic acid, punicic acid, α-elaeostearic acid, β-elaeostearic acid, and mixtures thereof.

5. The sulphosuccinate according to claim 1, wherein R is selected from sulphosuccinic acid radicals of the formula IIa or IIb.

6. The sulphosuccinates according to claim 1, wherein R$^5$ is selected from sulphomethylsuccinic acid radicals of the formula IIc or IId.

7. The sulphosuccinate according to claim 1, wherein R$^4$=the acyl radical of a natural fatty acid selected from the group consisting of caprylic acid, capric acid, lauric acid, and coconut fatty acid mixtures and R$^5$ is selected from sulphosuccinic acid radicals of the formula IIa or IIb.

8. A process for the preparation of a polyglycerol partial ester-based sulphosuccinate comprising the process steps:
A) reacting a polyglycerol having a degree of polymerization of 2 to 16 with 20 to 80 mol per cent, based on the polyglycerol, of one or more saturated or partially unsaturated carboxylic acids containing 6-22 carbon atoms which may be substituted by hydroxyl groups,
B) selecting from at least one of the process steps
B1) reacting with 30-600 mol per cent of maleic anhydride and/or itaconic anhydride, based on the polyglycerol, and
B2) reacting with 30-600 mol per cent of itaconic acid, based on the polyglycerol,
C) sulphonating with alkali metal, alkaline earth metal and/or ammonium sulphite salts and optionally
D) purification of the sulphosuccinates based on polyglycerol partial esters.

9. The process according to claim 8, wherein in process step A), the polyglycerol is reacted with 10-50 per cent by weight, based on the polyglycerol, of at least one carboxylic acid.

10. The process according to claim 8, wherein, in process step A), the polyglycerol has an average degree of polymerization n of 2-11.

11. The process according to claim 8, wherein, in process step A), fatty acids selected from the group consisting of caproic acid, oenanthic acid, caprylic acid, pelargonic acid, capric acid, lauric acid, myristic acid, pentadecanoic acid, palmitic acid, margaric acid, stearic acid, undecylenic acid, myristoleic acid, palmitoleic acid, petroselic acid, oleic acid, elaidic acid, vaccenic acid, linoleic acid, α-linolenic acid, γ-linolenic acid, calendic acid, punicic acid, α-elaeostearic acid and β-elaeostearic acid, and mixtures of thereof are used.

12. The process according to claim 8, wherein, in process step B), maleic anhydride or itaconic anhydride is used.

13. The process according to claim 8, wherein process step B2) is carried out with process step A) as a one-pot synthesis.

14. The process according to claim 8, wherein, in process step A), at least one carboxylic acid selected from caprylic acid, capric acid, lauric acid and coconut fatty acid mixtures and, in process step B), maleic anhydride according to B1) are used.

15. A formulation comprising at least one sulphosuccinate according to claim 1.

16. The formulation according to claim 15, wherein said formulation is essentially sulphate-free and essentially free from alkoxylated compounds.

17. The formulation according to claim 15, wherein said formulation is essentially polyglycol ether-free and essentially free from alkoxylated compounds.

18. The formulation according to claim 15, wherein said formulation is essentially sulphate-free, essentially polyglycol ether-free and essentially free from alkoxylated compounds.

* * * * *